(12) United States Patent
Cotter et al.

(10) Patent No.: US 10,799,260 B2
(45) Date of Patent: Oct. 13, 2020

(54) SHEAR STRESS ULTRASONIC CUTTING BLADE

(71) Applicant: Integra LifeSciences (Ireland) Ltd., Tullamore (IE)

(72) Inventors: Daniel J. Cotter, North Easton, MA (US); Prakash Manandhar, Lawrence, MA (US)

(73) Assignee: Integra LifeSciences (Ireland) Ltd., Tullamore (IE)

( * ) Notice: Subject to any disclaimer, the term of this patent is extended or adjusted under 35 U.S.C. 154(b) by 328 days.

(21) Appl. No.: 15/243,934

(22) Filed: Aug. 22, 2016

(65) Prior Publication Data

US 2016/0374706 A1    Dec. 29, 2016

Related U.S. Application Data

(60) Continuation-in-part of application No. 14/010,523, filed on Aug. 26, 2013, now Pat. No. 9,170,870, which is a continuation of application No. 13/325,999, filed on Dec. 14, 2011, now Pat. No. 8,518,066, which is a division of application No.
(Continued)

(51) Int. Cl.
*A61B 17/32* (2006.01)
*A61B 17/14* (2006.01)

(52) U.S. Cl.
CPC ...... *A61B 17/320068* (2013.01); *A61B 17/14* (2013.01); *A61B 2017/32007* (2017.08); *A61B 2017/320074* (2017.08); *A61B 2017/320078* (2017.08); *A61B 2017/320084* (2013.01)

(58) Field of Classification Search
CPC ........... A61B 17/320068; A61B 2017/320069; A61B 2017/320072; A61B 2017/320074; A61B 2017/320075; A61B 2017/320077; A61B 2017/320082; A61B 17/320092; A61B 2017/320093; A61B 17/3201; A61B 17/3209; A61B 17/32093; A61B 17/142; A61B 17/144; B23D 61/006; B23D 61/12; B23D 61/121; B23D 61/122;
(Continued)

(56) References Cited

U.S. PATENT DOCUMENTS

| | | | | |
|---|---|---|---|---|
| 829,158 | A * | 8/1906 | Keepfer | ............... B23D 61/123 30/502 |
| 2,112,271 | A * | 3/1938 | Dalkowitz | ............. D03D 39/24 139/44 |

(Continued)

*Primary Examiner* — Tan-Uyen T Ho
*Assistant Examiner* — Charles M Wei
(74) *Attorney, Agent, or Firm* — Thomas A. Runk; Brooks Kushman P.C.

(57) ABSTRACT

An ultrasonic horn for use with an ultrasonic surgical handpiece including a resonator comprises a linear cutting blade at the distal end of a horn body. The linear cutting blade includes adjacent side-by-side rows of teeth each of which includes a land through which ultrasonic energy is propagated outwardly from the distal end. The lands of the rows of teeth are angled so that the propagated ultrasonic energy of one plurality of lands intersects the propagated ultrasonic energy from the other row of lands. Shear stress fields are developed at the intersections of the ultrasonic energy that will perform the cutting function on target tissue. An irrigation arrangement is also disclosed.

23 Claims, 9 Drawing Sheets

Related U.S. Application Data

12/395,417, filed on Feb. 27, 2009, now Pat. No. 8,118,823.

(60) Provisional application No. 61/061,055, filed on Jun. 12, 2008.

(58) Field of Classification Search
CPC ...... B23D 61/126; B23D 61/14; B23D 61/16; B21D 61/123; B21D 61/128
See application file for complete search history.

(56) References Cited

U.S. PATENT DOCUMENTS

| | | | | |
|---|---|---|---|---|
| 3,748,738 | A * | 7/1973 | Alexander | B23D 51/025 30/394 |
| 3,946,778 | A * | 3/1976 | Knuth | B23D 49/14 30/501 |
| 4,423,553 | A * | 1/1984 | Miyawaki | B23D 61/121 30/355 |
| 5,306,285 | A * | 4/1994 | Miller | B23D 61/006 30/355 |
| 5,423,845 | A * | 6/1995 | McDaniel | B23D 61/121 30/355 |
| 5,695,510 | A * | 12/1997 | Hood | A61B 17/320068 30/355 |
| 6,379,371 | B1 | 4/2002 | Novak et al. | |
| 6,443,969 | B1 | 9/2002 | Novak et al. | |
| D667,117 | S * | 9/2012 | Darian | D24/144 |
| 8,382,782 | B2 | 2/2013 | Robertson et al. | |
| 8,894,673 | B2 | 11/2014 | Darian | |
| 9,095,367 | B2 | 8/2015 | Olson et al. | |
| 9,119,658 | B2 | 9/2015 | Paraschiv et al. | |
| 9,351,754 | B2 | 5/2016 | Vakharia et al. | |
| 9,393,037 | B2 | 7/2016 | Olson et al. | |
| 2001/0039738 | A1* | 11/2001 | Bachta | B23D 49/11 30/517 |
| 2004/0030254 | A1* | 2/2004 | Babaev | A61B 17/320068 600/459 |
| 2005/0222598 | A1* | 10/2005 | Ho | A61B 17/32 606/171 |
| 2005/0257660 | A1* | 11/2005 | Hayden | B23D 61/121 83/846 |
| 2008/0172890 | A1* | 7/2008 | Shetterly | B23D 61/123 30/355 |
| 2008/0188878 | A1* | 8/2008 | Young | A61B 17/16 606/169 |
| 2009/0105740 | A1* | 4/2009 | Lee | B23D 49/11 606/177 |
| 2009/0293698 | A1* | 12/2009 | Tran | B23D 61/121 83/846 |
| 2011/0125174 | A1* | 5/2011 | Babaev | A61B 17/320068 606/169 |
| 2012/0130380 | A1* | 5/2012 | Babaev | A61B 17/144 606/82 |
| 2013/0204255 | A1* | 8/2013 | Milburn | A61B 17/142 606/82 |
| 2015/0266119 | A1* | 9/2015 | Christensen | B23D 61/121 83/848 |
| 2015/0336189 | A1* | 11/2015 | Zhou | B23D 49/006 30/369 |
| 2016/0128716 | A1* | 5/2016 | Cao | A61B 17/320068 606/84 |
| 2017/0014152 | A1* | 1/2017 | Noui | A61B 17/320068 |
| 2017/0340339 | A1* | 11/2017 | Madan | A61B 17/1644 |

\* cited by examiner

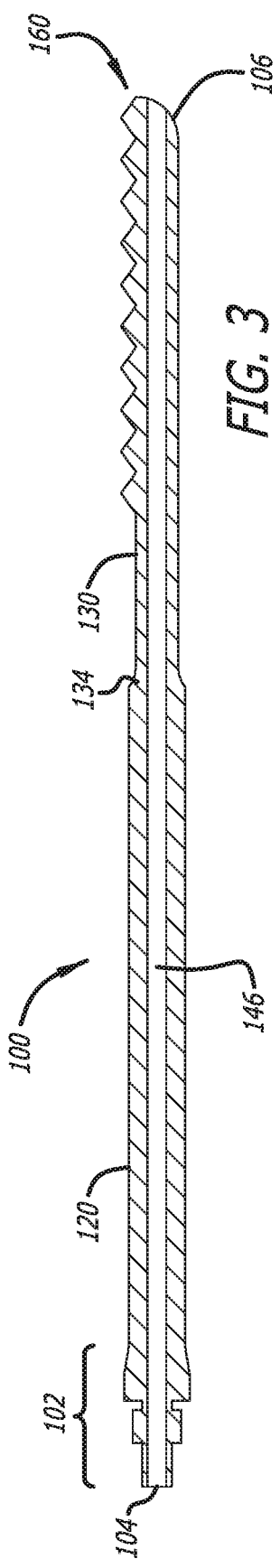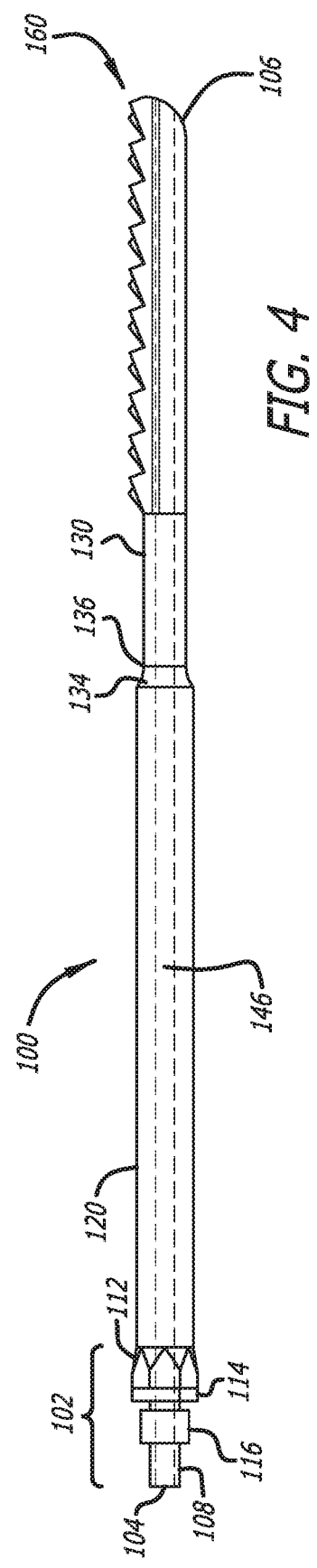

SHEAR STRESS ULTRASONIC CUTTING BLADE

CROSS-REFERENCES TO RELATED APPLICATIONS

This application is a continuation-in-part of U.S. application Ser. No. 14/010,512, filed Aug. 26, 2013, now U.S. Pat. No. 9,421,027, which was a continuation of application Ser. No. 13/325,999, filed Dec. 14, 2011, now U.S. Pat. No. 8,518,066, which is a division of application Ser. No. 12/395,417, filed on Feb. 27, 2009, now U.S. Pat. No. 8,118,823, that claims the benefit of Provisional Application No. 61/061,055, filed Jun. 12, 2008, all of which are incorporated herein by reference.

BACKGROUND

The invention relates generally to ultrasonic surgical devices, and more particularly to an ultrasonic cutting blade.

Devices that effectively utilize ultrasonic energy for a variety of applications are well known in a number of diverse arts. One of these devices is an ultrasonic horn used for the removal of tissue. The Ampulla or Gaussian profile was published by Kleesattel as early as 1962, and is employed as a basis for many ultrasonic horns in surgical applications including devices described in U.S. Pat. No. 4,063,557 to Wuchinich, et al, 1977, and U.S. Pat. No. 6,214,017 to Stoddard, et al, 2001 for use in ultrasonic aspiration. The Gaussian profile is used in practice to establish and control the resonance and mechanical gain of horns. A resonator, a connecting body, and the horn act together as a three-body system to provide a mechanical gain, which is defined as the ratio of output stroke amplitude of the distal end of the tip to the input amplitude of the resonator. The mechanical gain is the result of the strain induced in the materials of which the resonator, the connecting body, and the ultrasonic horn are composed.

A magnetostrictive transducer coupled with the connecting body functions as a first stage of the booster horn with a mechanical gain of about 2:1, due to the reduction in area ratio of the wall of the complex geometry. The major diameter of the horn transitions to the large diameter of the Gaussian segment in a stepped-horn geometry with a gain of as large as about 5:1, again due to reduction in area ratio. The uniform strain along the length of the Gaussian provides multiplicative gain of typically less than 2:1. Thus, the application of ultrasonically vibrating surgical devices used to fragment and remove unwanted tissue with significant precision and safety has led to the development of a number of valuable surgical procedures. Accordingly, the use of ultrasonic aspirators for the fragmentation and surgical removal of tissue from a body has become known. Initially, the technique of surgical aspiration was applied for the fragmentation and removal of cataract tissue. Later, such techniques were applied with significant success to neurosurgery and other surgical specialties where the application of ultrasonic technology through a handheld device for selectively removing tissue on a layer-by-layer basis with precise control has proven feasible.

Certain devices known in the art characteristically produce continuous vibrations having substantially constant amplitude at a predetermined frequency (i.e. 20-36 kHz). Certain limitations have emerged in attempts to use such devices in a broad spectrum of surgical procedures. For example, the action of a continuously vibrating tip may not have an adequate effect in breaking up certain types of body tissue, more elastic tissue, bone, etc. Because the ultrasonic frequency is limited by the physical characteristics of the handheld device, only the motion available at the tip provides the needed motion to break up a particular tissue. All interaction with the tissue is at the tip, some is purely mechanical, and some is ultrasonic. Some teach in the art that interaction with the tissue at the tip distal and is due only to mechanical interaction. To others, it is clear from experimental results that acoustic power is propagated to the load to aid in tissue fragmentation, emulsification, and aspiration. In any case, the devices have limitations in fragmenting some tissues. The limited focus of such a device may render it ineffective for certain applications due to the vibrations which may be provided by the handheld device. For certain medical procedures, it may be necessary to use multiple hand held devices or it may be necessary to use the same console for powering different handheld devices.

Certain devices known in the art characteristically produce continuous vibrations having substantially constant amplitude at a frequency of about 20 to about 55 kHz. Amplitude of transducer-surgical tip systems decreases with increasing frequency because maximum stress in the material of the horns is proportional to amplitude times frequency, and the material must be maintained to an allowed fraction of its yield strength to support rated life in view of material fatigue limits. For example, U.S. Pat. Nos. 4,063, 557, 4,223,676 and 4,425,115 disclose devices suitable for the removal of soft tissue which are particularly adapted for removing highly compliant elastic tissue mixed with blood. Such devices are adapted to be continuously operated when the surgeon wishes to fragment and remove tissue, and generally is operated by a foot switch.

A known instrument for the ultrasonic fragmentation of tissue at an operation site and aspiration of the tissue particles and fluid away from the site is the CUSA EXcel® Ultrasonic Surgical Aspirator (Integra LifeSciences Corporation, Plainsboro, N.J.). When the longitudinally vibrating tip in such an aspirator is brought into contact with tissue, it gently, selectively, and precisely fragments and removes the tissue. The CUSA® transducer amplitude can be adjusted independently of the frequency and this amplitude can be maintained under load depending on reserve power of the transducer. In simple harmonic motion devices, the frequency is independent of amplitude. Advantages of this unique surgical instrument include minimal damage to healthy tissue in a tumor removal procedure, skeletoning of blood vessels, prompt healing of tissue, minimal heating or tearing of margins of surrounding tissue, minimal pulling of healthy tissue, and excellent tactile feedback for selectively controlled tissue fragmentation and removal.

In an apparatus that fragments tissue by the ultrasonic vibration of a tool tip, efficiency of energy utilization is optimized when the transducer which provides the ultrasonic vibration operates at resonant frequency. The transducer and surgical tip design establishes the resonant frequency of the system, while the generator tracks the resonant frequency and produces the electrical driving signal to vibrate the transducer at the resonant frequency. However, changes in operational parameters, such as changes in temperature, thermal expansion and load impedance, result in deviations in the resonant frequency. Accordingly, controlled changes in the frequency of the driving signal are required to track the resonant frequency. This is controlled automatically in the generator.

Conventional ultrasonic surgical aspirating tips employed in surgery for many years typically present a longitudinally vibrating annular surface with a central channel providing suction or aspiration, which contacts tissue and enables fragmentation via described mechanisms of mechanical impact (momentum), cavitation, and ultrasound propagation. Mechanical impact may be most useful in soft tissue and cavitation clearly contributes to the fragmentation of tenacious and hard tissue in situations where liquids are present and high intensity ultrasound exceeds the cavitation threshold.

Ultrasound propagation is concerned with the transmission of pressure across the boundary of a surgical tip and tissue, which leads to the propagation of pressure and, perhaps more importantly, particle displacement. Acoustic impedance is the total reaction of a medium to acoustic transmission through it, represented by the complex ratio of the pressure to the effective flux, that is, particle velocity times surface area through the medium. As discussed in the classic text of Krautkramer J. and Krautkramer H., *ULTRASONIC TESTING OF MATERIALS*, Berlin, Heidelberg, N.Y., 1983, for the case of a low to high acoustic impedance boundary, it may seem paradoxical that pressure transmitted can exceed 100% but that is what results from the build-up of pressure from a low to high acoustic impedance boundary. In the case of a high to low acoustic impedance mismatch, such as with a high impedance titanium ultrasonic horn to low impedance fibrous muscle, soft tissue, or water, the pressure transmitted decreases (e.g., less than 15% for titanium to fibrous muscle) and particle displacement increases (e.g., as great as 186% for titanium to muscle).

Conventional ultrasonic surgical aspirating tips have been found to be efficient in the removal of soft tissue, and with emergent bone tips, applicable to the removal of hard tissue; however, some fibrous, elastic, and tenacious tissues persist in difficulty of removal. It has been found that using such conventional ultrasonic horns and devices that employ only the effects of intensification of ultrasound or sharpened edges to remove bovine fibrous muscle tissue, leaves a fibrous elastic skeleton. Thus, there remains a need for ultrasonic surgical devices with innovative aspiration tips that allow for more effective removal of fibrous tissue via the enhanced utilization of ultrasound fragmentation effects.

It is known that materials often fail, fracture, tear, or rupture, more readily as a result of a shear force rather than in tension or compression. Common examples include paper, garden bushes, hair, cloth, steel shear bolts or pins, and collagenous materials. A thin fibrous sheet of paper can be pulled or snapped with a greater tension force, but it can much more easily be ripped by the fingers applying light forces in opposite directions (shear). Likewise, scissors readily cut paper by employing a shear force concentrated by opposing edges of the scissors. Studies of mechanical behavior of materials have shown that biologic tissue is viscoelastic material, meaning that it has a time-dependent stress-strain relationship. The effect of the strain rate on the material is critical to causing fragmentation. The ultrasonic horn of the present invention evolved from imagining innovative ways of introducing scissor or shear ultrasonic effects with a surgical aspirating tip.

Cutting living bone in the field of orthopedics is performed in many procedures. Such procedures include grafting healthy bone into areas damaged by disease, or the correction of various congenital abnormalities. Mechanical bone saws have been traditionally used. While they are functional, there are disadvantages. With some it is difficult to initiate a cut. A cut must start from an edge or from a starting hole. When a rotary blade is used, binding of the rotary blade can occur unless the blade is moved in a straight line through the bone. Creating a curved cut can be limited by the configuration of the blade that is chosen. The use of relatively thick blades is likely to remove viable undamaged bone during the cutting procedure, which is undesirable. A goal in many procedures is to cut a width that is as small as possible.

Also, mechanical saw blades can develop heat during use which can cause necrosis of the surrounding tissue, another very undesirable effect. Heat can lessen the strength of the bone also. Irrigation with cooling fluid is often used when cutting bone and this can assist in avoiding necrosis. However, it is difficult to uniformly cool the tool.

One advance in the field has been the use of ultrasonic surgical instruments to take the place of traditional bone saws or scalpels. These devices have proven to be superior to the traditional saws in several aspects, such as the thinner size of their cutting tool, lowered noise levels, and their ability to more easily make complex geometric cuts. Since ultrasound energy dissipates in soft tissue (dura, nerves, vascular structures, etc.) this device is the ideal tool for bone removal in critical areas. However, some of those available today still rely at least part of the tool having a saw blade that can mechanically cut the bone. This creates heat which can be detrimental to the target bone as described above. The ultrasound tools are able to effectively use irrigation during the cutting process which will lessen the amount of heat transferred to viable bone tissue.

Soft tissue has elastic properties that allow it to deform and rebound without failure to its integrity. Osteotomies can be performed in close proximity to delicate structures. Tissue response to the ultrasound action differs by tissue density, collagen content, blade pressure, and exposure time. Integrated and continuous irrigation is used to compensate for thermal effects.

Another need has been shown for an ultrasonic cutting blade that is able to cut laterally (also referred to as "transversely"), that is, in a direction substantially perpendicular to the axis of the blade, and thus substantially perpendicular to the direction of propagation of ultrasonic compression waves, in addition to cutting in a forward or distal direction away from the user. A further need that exists is for an ultrasonic cutting blade that, in addition to cutting in a forward or distal direction away from the operator of the instrument, is able to cut rearward, that is in a proximal direction towards the operator.

Hence, those skilled in the art have recognized a need for an improved surgical device and method with innovative aspiration tips that allow for more effective removal of fibrous tissue via the enhanced utilization of ultrasound fragmentation effects. There is also a recognized need for an ultrasound device with provides irrigation cooling to protect tissue. A further need has been identified for an ultrasound cutting device that allows more effective removal of fibrous and tenacious tissues. Yet a further need has been identified for a cutting device that can be used in different directions. The present invention fulfills these needs and others.

SUMMARY OF THE INVENTION

Briefly and in general terms, the present invention is directed to an apparatus and an associated method of fragmenting and removing target tissue by the introduction of shear stress and the utilization of high strain rates associated with ultrasound. In more detailed aspects, the invention is directed to an ultrasonic horn configured for use with an ultrasonic surgical handpiece having a resonator that generates ultrasonic waves, the ultrasonic horn comprising a body member having a proximal end, a distal end, and a longitudinal axis, the proximal end being adapted to connect to the handpiece and receive ultrasonic waves from the handpiece, and the body member configured to conduct the received ultrasonic waves to the distal end, an ultrasonic blade located at the distal end, the ultrasonic blade being non-annular and having a linear cutting surface on which are located two teeth positioned adjacent each other, each tooth having a root located at the cutting surface and a land located outward from the cutting surface, each land configured to propagate ultrasonic energy outwardly from the distal end, and wherein the land of the first tooth and the land of the second tooth are located and oriented in relation to each other so that the respective ultrasonic energy propagated outwardly by both lands intersect to create a shear stress field.

In more detailed aspects, the linear cutting surface has a first width on which the adjacent teeth are located, and wherein the blade has material under the linear cutting surface that is undercut whereby a width of the blade at the undercut is less than the width of the blade at the cutting surface. The first tooth is located on the cutting surface so that the first land is extending in the distal direction. The roots of the first and second teeth are transversely aligned with each other across the longitudinal axis at the cutting surface. An angle of the land of the first tooth and an angle of the land of the second tooth are different. The roots of the first and second teeth are offset from each other across the longitudinal axis at the cutting surface. The angle of the land of the first tooth and the angle of the land of the second tooth are opposite angles.

In yet another aspect, the first tooth is located at the cutting surface and oriented at an angle to the longitudinal axis so that ultrasonic energy propagating from the land of the first tooth intersects ultrasonic energy propagating from the face of the second tooth so that a shear field is located transverse to the longitudinal axis.

In further aspects, the first tooth is located in a first linear row of a plurality of teeth that is located at the cutting surface, each of the teeth in the first row of teeth having a root and a land wherein the lands have angles, the second tooth is located in a separate second linear row of a plurality of teeth that is located at the cutting surface adjacent the first row of teeth, each of the teeth in the second row of teeth having a root and a land wherein the lands have angles, and wherein the angles of the lands in the first and second rows are selected to be different so that ultrasonic energy propagating through the rows of teeth and outwardly through the lands will intersect to result in a plurality of shear fields. The lands of the teeth in the first row extend in the distal direction and the lands of the teeth in the second row extend in the proximal direction. The roots of the teeth in the first row are aligned transversely with the roots of the teeth in the second row and the lands of the first row have a different angle from the lands in the second row.

In other more detailed aspects, the first and second rows are parallel with the longitudinal axis and are positioned on either side of the longitudinal axis in forming the linear cutting surface of the blade. The roots of the teeth in the first row are offset from the roots of the teeth in the second row and the lands of the first row have the same but opposite angle in respect to the lands in the second row.

In additional aspects, there is provided an ultrasonic horn configured for use with an ultrasonic surgical handpiece having a resonator that generates ultrasonic waves, the ultrasonic horn comprising a body member having a proximal end, a distal end, and a longitudinal axis, the proximal end being adapted to connect to the handpiece and receive ultrasonic waves from the handpiece, and the body member configured to conduct the received ultrasonic waves to the distal end, and an ultrasonic blade located at the distal end, the ultrasonic blade being non-annular and having a linear cutting surface on which are located two linear rows of teeth, each row having a plurality of teeth, the rows being positioned on either side of the longitudinal axis adjacent each other, each tooth having a root located at the cutting surface and a land located outward from the cutting surface, each land configured to propagate ultrasonic energy outwardly, wherein the lands of the first row of teeth and the lands of the second row of teeth are located and oriented in relation to each other so that the respective ultrasonic energy propagated outwardly by the lands of one row intersect with the ultrasonic energy propagated outwardly by the lands of the other row to create shear stress fields.

In related detailed aspects, the locations of the roots in the first linear row of teeth are offset from the locations of the roots in the second linear row of teeth; and the angles of the lands in the first row of teeth are opposite the angles of the lands in the second row of teeth. The locations of the roots in the first linear row of teeth are aligned with the locations of the roots in the second linear row of teeth, and the angles of the lands in the first row of teeth are different from the angles of the lands in the second row of teeth.

In method aspects in accordance with the invention, there is provided a method of creating a shear stress field with ultrasonic energy comprising conducting ultrasonic energy through a body member from a proximal end of the body member to a distal end of the body member, the body member having a longitudinal axis and propagating the conducted ultrasonic energy outwardly from the distal end of the body member through a first tooth and a second tooth that are both mounted to a cutting surface of a non-annular linear blade located at the distal end and are positioned adjacent each other, each tooth having a root located at the cutting surface and a land located outward from the cutting surface, wherein the step of propagating comprises propagating ultrasonic energy outwardly by each land in a direction that intersects propagated energy by the other land to thereby form a shear stress field.

In more detailed method aspects, the propagating step further includes propagating the conducted ultrasonic energy outwardly from the distal end of the body member through lands of a first row of teeth and through lands of a second row of teeth, both rows of teeth being located separately at the non-annular, linear cutting surface and are positioned adjacent each other in a side-by-side arrangement. The lands of one row of teeth have a first angle and the lands in the other row of teeth have a second angle that is opposite the first angle.

Other features and advantages of the present invention will become more apparent from the following detailed description of the invention, when taken in conjunction with the accompanying exemplary drawings.

BRIEF DESCRIPTION OF THE DRAWINGS

Embodiments of the presently disclosed shear stress ultrasonic horn having a cutting blade are described herein with reference to the illustrative drawings, in which:

FIG. 3 shows a general cross-sectional view of the horn embodiment of FIG. 1 showing a channel formed completely through the horn including the distal tip cutting blade in this embodiment, the channel being usable for aspiration;

FIG. 4 is a side view of the horn of FIG. 1 showing further detail of the adapter configuration at the proximal end of the horn and showing in dashed lines the channel formed through the entire length of the horn that is usable for aspiration;

DETAILED DESCRIPTION OF PREFERRED EMBODIMENTS

Figure 1:
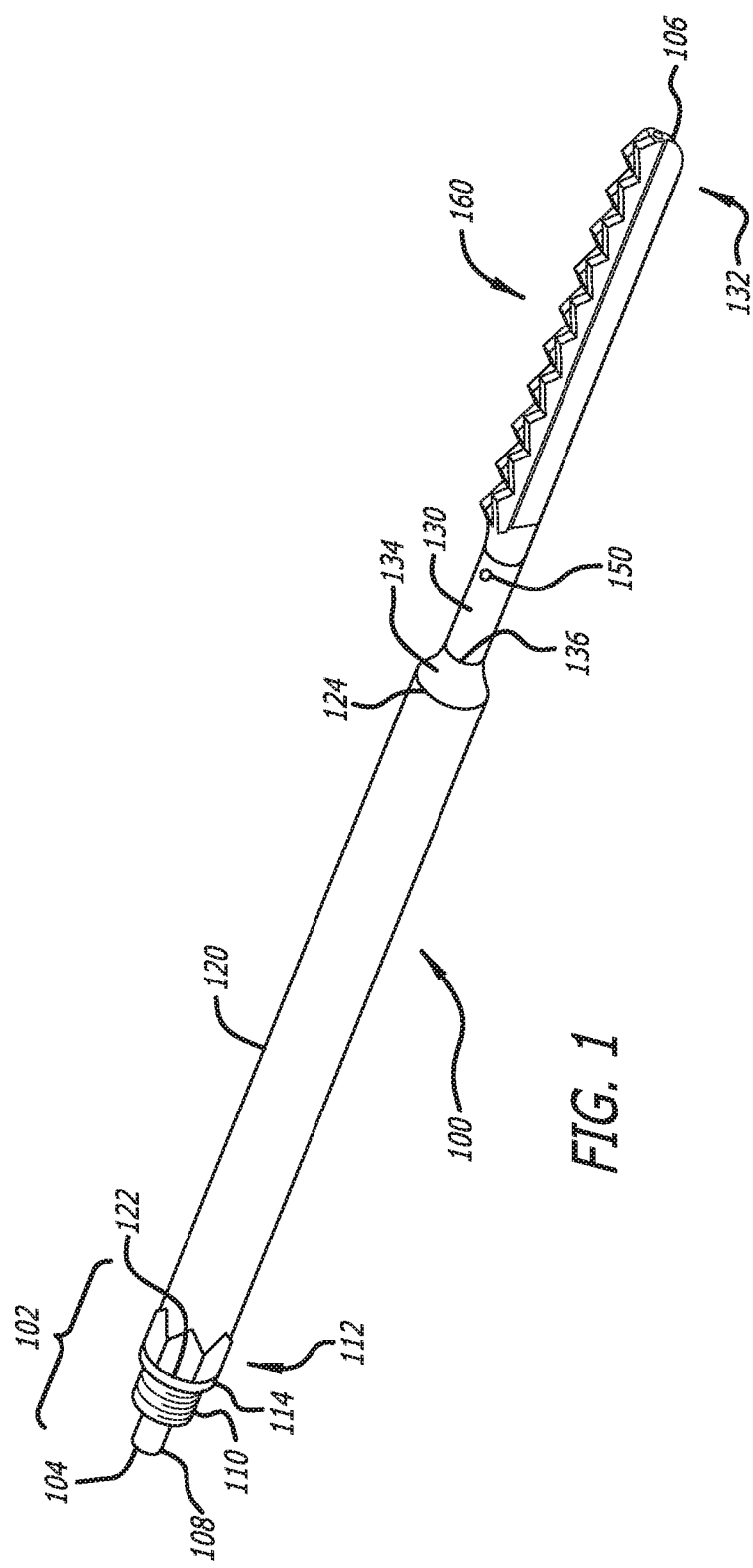
FIG. 1 is a perspective view of an ultrasonic horn in accordance with aspects of the present invention in which the horn includes an extension member, an elongated member, and a distal end having a linear cutting blade of a particular configuration for establishing shear stress in target material, and further includes an adapter at its proximal end for connection with an ultrasonic energy source.

Turning now in more detail to the figures, in which like reference numerals designate like or corresponding elements among the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic aspirating tip," "aspirating tip," "ultrasonic surgical tip," and "surgical tip" are used herein interchangeably.

Referring now to FIG. 1 in more detail, there is shown an ultrasonic horn 100, in accordance with one embodiment of the present disclosure. The ultrasonic horn is adapted for use in an ultrasonic surgical system having an ultrasonic handpiece. An example of such an ultrasonic surgical system is disclosed in U.S. Pat. No. 6,214,017 to Stoddard et al., the entire contents of which are incorporated herein by reference. Alternatively, the ultrasonic horn 100 may be adapted for use with the ultrasonic surgical system disclosed in U.S. Pat. No. 4,063,557 to Wuchinich et al., the entire contents of which are incorporated herein by reference.

The ultrasonic horn 100 of FIG. 1 includes a proximal end 104 and a distal end 106. At the proximal end the horn comprises an adapter 102 that includes, extending from the proximal end 104 towards the distal end 106, a shaft 108, a threaded member 110, and a flange 112 terminating at the distal end 106. The flange 112 includes a leading edge 114.

Figure 2:
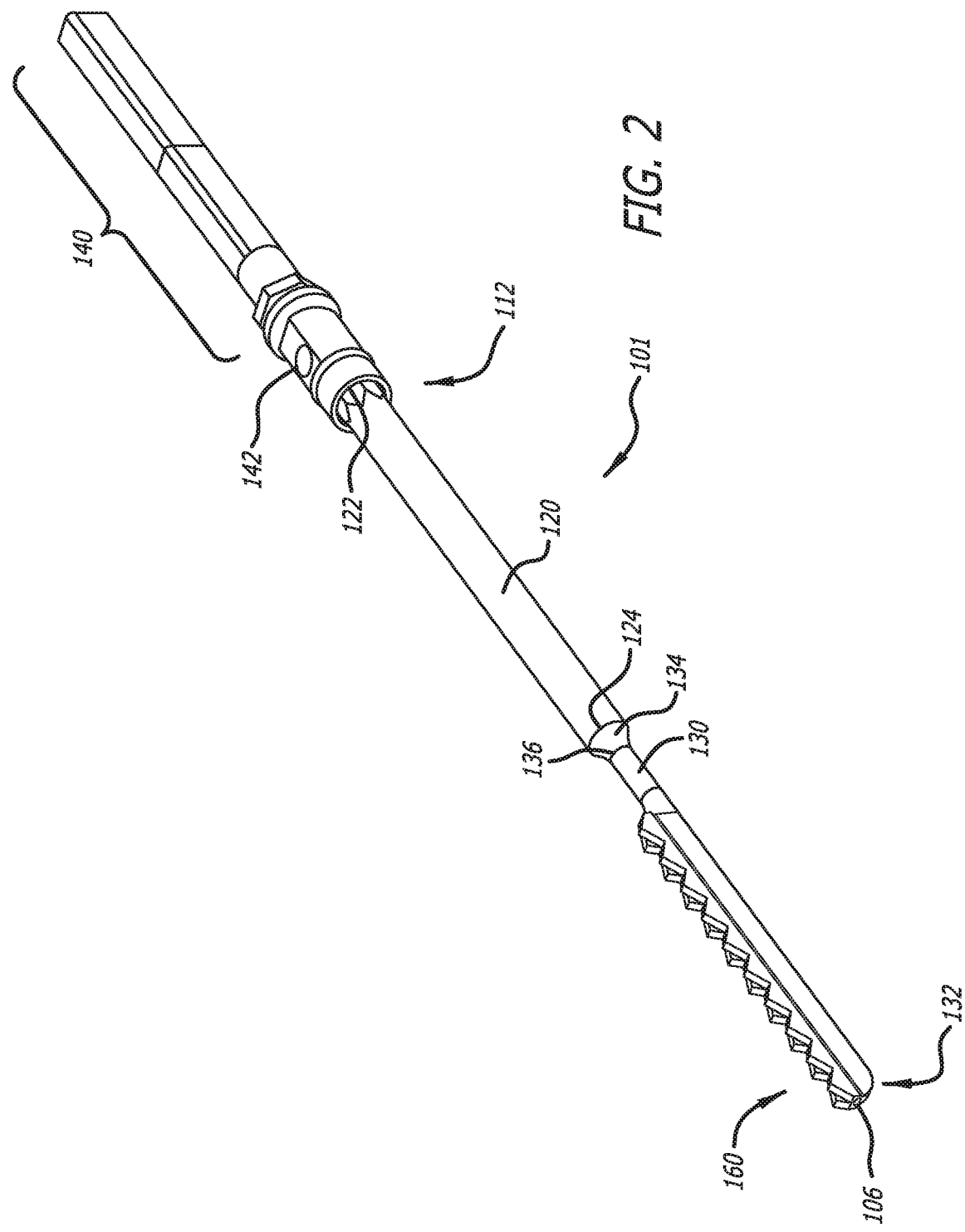
FIG. 2 presents a perspective view of an ultrasonic horn similar to FIG. 1 having the cutting blade located at its distal end, the horn also showing actual connection to an ultrasonic energy generator at its proximal end.

The proximal end 104 of the adapter 102 is configured to connect the ultrasonic horn 100 to an ultrasonic handpiece or resonator. Referring also now to FIG. 2, the connection of an ultrasonic horn to a resonator 140 is shown. FIG. 2 shows a horn 101 similar to the horn 100 of FIG. 1 with the exception that the horn 101 of FIG. 2 is curved at an angle of approximately 13°. The base designs of such horns include both curved and straight surgical tips; i.e. the profiles may be the same. The surgical curved tips are bent on a mandrel following machining. The bend can be about 13° or less.

Curved surgical tips are often preferred because the handpiece is moved out of the field of view of the microscope used by the surgeon viewing the distal end. The curve in the embodiment of FIG. 2 is formed in an extension member 120 of the horn, as described below in further detail.

The resonator 140 is connected to the adapter 102 of the horn through a connecting body 142 in this embodiment. As used herein, the term "resonator" refers to what is often referred to in the literature as an ultrasonic handpiece. The resonator is typically a laminated core-stack of Permanickel. Those skilled in the art will recognize that the threaded member 110 is identified herein in one embodiment as an externally threaded member for connection to internal threads of the connecting body 142 and/or to an ultrasonic resonator 140 but that other connection types can be implemented to connect to the connecting body and/or ultrasonic resonator. Such connection types include but are not limited to welds, socket couplings, and compression couplings. Because such resonators and connections are well known to those skilled in the art, no further details are provided here.

The ultrasonic horns 100 and 101 both include an extension member 120 having a proximal end 122 that coincides with the flange 112 of the adapter 102. The extension member 120 also has a distal end 124. The horn further comprises an elongated member 130 with a distal tip 132 at the distal end 106 of the horn. The distal end 124 of the extension member terminates in a transition segment 134 to the elongated member 130 in this embodiment. The proximal end 136 of the elongated member is located at the distal side of the transition segment 134 while the distal end of the extension member is located at the proximal side of the transition segment. The distal end of the elongated member 130 is configured as the distal tip 132.

The connecting body 142 is configured to connect the resonator 140 to the horn 101 so that ultrasonic energy may be applied to the horn and conducted to a target site. In one embodiment, the resonator 140 includes a magnetostrictive transducer, although other transducer types can be included such as a piezoelectric transducer. The resonator 140 is supplied power from a power generator (not shown) such that the resonator 140 operates at a target frequency, e.g., in the range of about 23,000 Hz (23 kHz), 36,000 Hz (36 kHz) or other. Utilizing a piezoelectric transducer will provide similar ultrasonic properties and alternate frequencies for higher stroke and power (e.g., 23 kHz and 24 kHz devices). It is important to note that use of alternative transducers or ultrasonic frequencies will not substantially deviate from the innovative principles of the shear stress ultrasonic horn disclosed herein. In one embodiment, the ultrasonic horns 100 and 101 are made of titanium, although other materials such as stainless steel may be used. In a preferred embodiment, the titanium ultrasonic horn is nitride coated to improve hardness and improve wear resistance.

As best seen in FIG. 3, which is a longitudinal cross-sectional view of the ultrasonic horn 100 of FIG. 1, an internal channel 146 is formed longitudinally through the entire horn, i.e., from the distal end 106 to the proximal end 104. The channel terminates in the connecting body 102, and does not continue into the resonator (not shown). In some embodiments, the channel may be coupled to a side port or other device to introduce fluid into the channel (irrigation) or withdraw fluid from the channel by means of suction or vacuum (aspiration). In some implementations, the central channel supports aspiration or suction of tissue as it is broken into particles by the horn. The internal channel can provide suction when connected with a vacuum source at the console. The suction can also be used to control the position of target tissue. For example, suction may be used to draw target tissue to the distal end 160 of the horn for coupling and contact to the tissue for efficient fragmentation. The internal channel shown and described herein may also be used to aid in cooling, where irrigation liquid is caused to flow through the channel.

The internal channel 146 also affords greater mechanical gain for the horn 100 and 101 because the gain is dependent on the reduction in area ratio of the thin walls. A purpose of the internal channel 146 is to support gain for surgical tips with the cutting blade distal end 160.

Referring now to FIG. 4, a side view of the ultrasonic horn 100 of FIG. 3 is shown with only the channel 146 shown in dashed lines. The adapter 102 is also shown. As is clearly shown in the dashed lines, the internal channel 146 is also formed within the adapter 102 and throughout the remainder of the horn 100.

In FIGS. 1 through 4, the horn is shown as being elongated. This is not meant to be limiting but only an embodiment. In other embodiments, the horn may not be elongated depending on the requirements of the application. As referred to herein, the part of the horn proximal to the distal end is referred to as a body member.

Figure 5A:
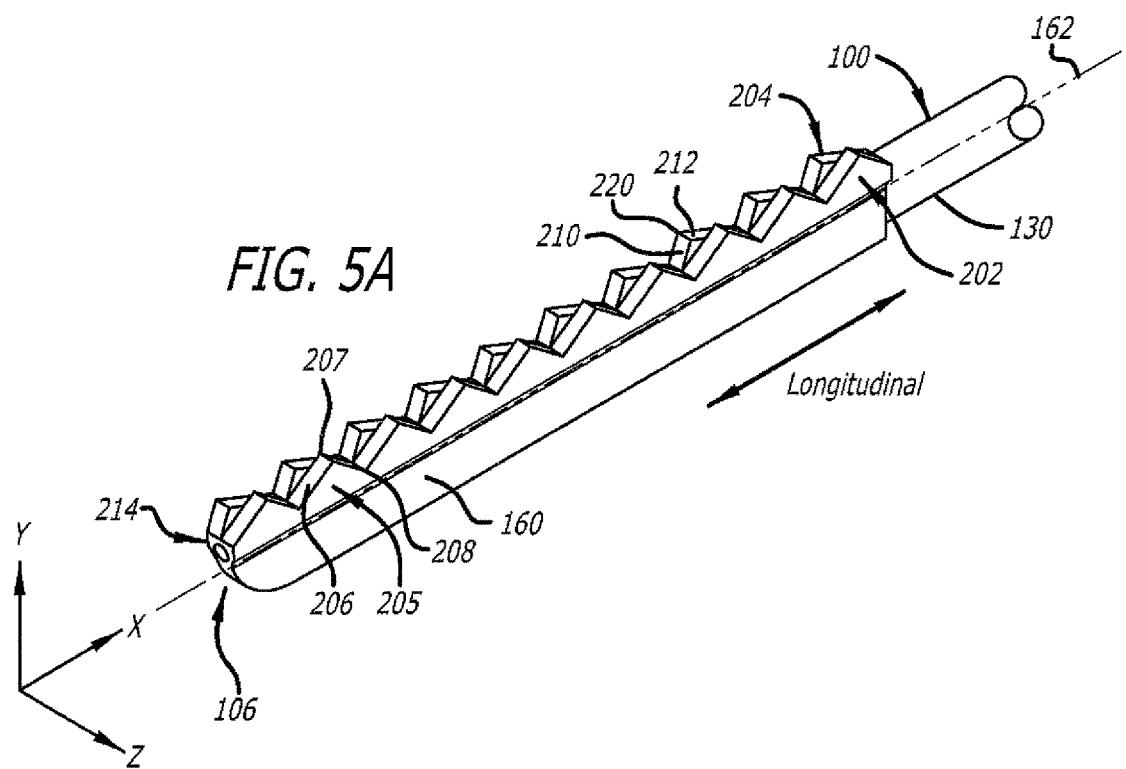
FIG. 5A is a perspective view of an embodiment of a shear stress ultrasonic linear cutting blade mounted at the distal end of the horns of FIGS. 1 and 2 showing a pair of adjacent separate rows of teeth located at the cutting surface of the cutting blade, each tooth having a land with the lands of one row having the same but opposite angle in respect to the lands of the other row with the roots of the teeth of one row being offset in respect to the roots of the teeth of the other row, the blade being undercut below the cutting surface, and further showing the distal opening of the internal aspiration channel.
Figure 5B:
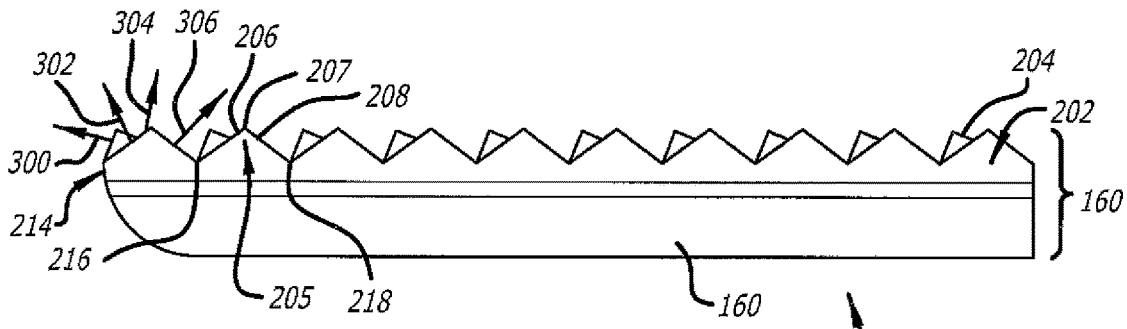
FIG. 5B is a side view of the shear stress ultrasonic cutting blade of FIG. 5A showing one row of teeth in the front and what can be seen of the second row of teeth in the back.

Referring now to FIG. 5A, there is shown a perspective, more detailed, view of an embodiment of a shear stress ultrasonic cutting blade 160 that is mounted at the distal end 106 of the horns 100 and 101 of FIGS. 1 and 2. FIG. 5A shows a configuration of features used to create shear stress in target tissue. In this embodiment, a pair of adjacent, but separate, rows of teeth 202 and 204 are provided to form the cutting blade 160. Each of the rows has a plurality of teeth lined up in parallel to the longitudinal axis 162 of the cutting blade in this embodiment. Each tooth in this embodiment has two lands with a peak in between. Each tooth also has two roots, one at the base of each land of the tooth. As an example, tooth 205 of the first row 202 of teeth has a distal land 206 and a proximal land 208 with a peak 207 in between at a position outward from the cutting surface 214. Two roots 216 and 218 of a single tooth 205 in the first row 202 are shown in FIG. 5B. Each of the teeth in the first row have like features.

Each of the teeth in the second row 204 of FIG. 5A also have like features with a distal land 210, a proximal land 212, and a peak 220 in between the two lands. Each tooth also has two roots (not shown) at the bottom of each land, which is at the cutting surface 214.

Figure 5C:
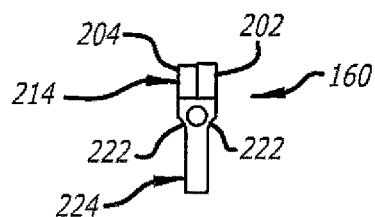
FIG. 5C is a front view of the shear stress ultrasonic cutting blade of FIGS. 5A and 5B showing the opening of the aspiration channel and the undercut of the blade under the cutting surface.

Referring briefly to FIG. 5C, a front view of the cutting blade 160 is shown. The blade includes a cutting surface 214 at which the rows of teeth 202 and 204 are located. The remainder of the blade is undercut 222 so that it will not cause the remainder 224 of the blade 160 to bind when cutting target tissue is being performed.

Referring back to FIG. 5B, ultrasonic energy is conducted through the horn 100 to the distal end 106. That ultrasonic energy is propagated outward from the horn through the lands of both rows 202 and 204 of teeth. Adjacent lands in this figure have different angles that is, a land in the first row 202 is adjacent a land in the second row 204. Both the distal lands of the adjacent teeth and the proximal lands of the adjacent teeth will have different angles. This is because the roots 216 and 218 of the teeth of the first row 202 are aligned with the roots 226 and 228 of the teeth of the second row 204 which can be seen in FIG. 5D. However, the locations of the peaks are different. In this embodiment, the peaks 207 of the teeth in the first row is centered and both the distal and proximal lands are at an angle of 45° to the cutting surface 214. However, the angles of the lands of the teeth in the second row are different than those of the first row. The peaks 236 of the teeth in the second row 204 are placed so that the distal land 210 has an angle of 60° with the cutting surface and the proximal land 212 has an angle of 30°. However the angles of both the distal land 206 and the proximal land 208 in the first row 202 is 45°. That results in a difference in angle between the ultrasonic energy propagating from both sets of adjacent lands of 15°. The propagating ultrasonic energy will intersect at those particular angles.

In FIG. 5B, the ultrasonic energy propagating 300 from the distal land of the most distal tooth of the second row will produce shear waves with the energy propagating 302 from the distal land of the most distal tooth in the first row when undergoing a longitudinal motion front stroke. Likewise the ultrasonic energy propagating 304 from the proximal land of the most distal tooth of the second row will produce shear waves with the energy propagating 306 from the proximal land of the most distal tooth in the first row when undergoing a longitudinal motion back stroke.

Using ultrasonic shear geometry to provide a cutting device that functions similarly to a saw or scalpel would be expected to have improved efficacy relative to existing devices. A cross-cut wood saw has teeth that enable efficient cutting both with or across the grains of wood. The teeth of a cross-cut saw are protruded, or bent off the center line. In the embodiment of FIG. 5A, shear stress is promoted by having the rows of teeth next to each other with an angle of a land in one row being next to a land of another angle located in the adjacent row, with adjacent rows of teeth, with lands of different angles.

These rows could be machined separately and brazed or silver soldered to an ultrasonic horn, or perhaps the horn can be machined as a contiguous solid body using an EDM (Electrode Discharge Machine) mask. It is believed by the inventors that the shear geometry can be powered by a stepped horn and perhaps a Gaussian horn. It is also believed that a ripple wave perpendicular to the teeth could be promoted to give the effect of protruding them relative to the longitudinal motion (transverse similar to a cross-cut).

Figure 6A:
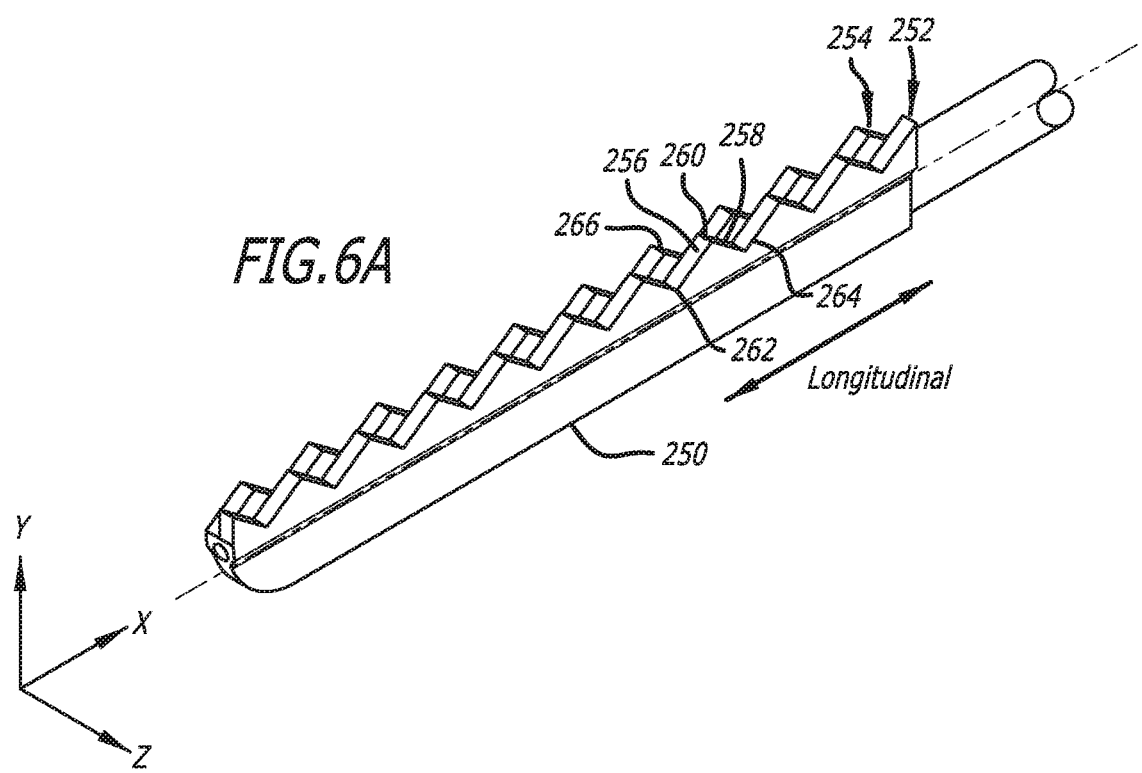
FIG. 6A is a perspective view of a different embodiment of a shear stress ultrasonic cutting blade mounted at the distal end of the horns of FIGS. 1 and 2 similar to that of FIG. 5A except that the teeth of this embodiment are all formed by triangular cuts with the rows being offset from each other.

FIG. 6A is a perspective view of a different embodiment of a distal tip cutting blade 250 mounted at the distal end of the horns of FIGS. 1 and 2 similar to that of FIG. 5A except that the teeth of this embodiment are all formed by triangular cuts with the rows being offset from each other. The ultrasonic shear stress cutting blade 250 has the same triangle cuts for all teeth, both first row 252 and second row 254. In order to make angular differences between the angles of the lands in the first row and the lands in the second row, the root positions and peak positions are offset. In this embodiment as shown more clearly in FIG. 6D, the peaks 270 of the teeth in the second row align with the roots 272 of the teeth in the first row. Thus the angular difference is 90° between all adjacent distal and proximal lands. This is shown in FIG. 6B where the energy propagated from the distal land 256 of the first row intersects the energy propagated from the proximal land 266 of the second row.

Figure 6B:
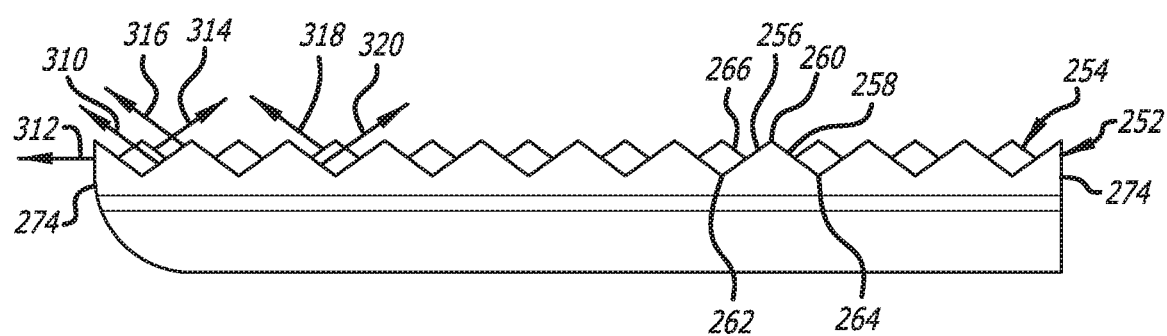
FIG. 6B is a side view of the shear stress ultrasonic cutting blade of FIG. 6A showing one row of teeth in the front and what can be seen of the second row of teeth in the back.

In FIG. 6B, the ultrasonic energy propagating 310 from the distal land of the most distal tooth of the second row will produce shear waves with the energy propagating 312 from the distal land of the most distal tooth in the first row when undergoing a longitudinal motion front stroke. The ultrasonic energy propagating 314 from the proximal land of the most distal tooth of the second row will produce shear waves with the energy propagating 316 from the distal land of the most second most distal tooth in the first row when undergoing either a longitudinal motion front or back stroke. Transverse motion may also be generated by the ultrasonic energy of 314 and 316. The same is true for the ultrasonic energy propagating 318 and 320 from lands in the front and back rows. Shear waves are created for front and back longitudinal strokes as well as transverse motion. Transverse motion is shown by the axis Z in FIG. 6A.

It has been found that adjacent lands of opposite angles promote refracted longitudinal waves propagating in different directions at the interface to the tissue to establish shear forces. Refracted longitudinal waves of different directions produce a shear stress field, especially at the intersection of opposite angled lands 266 and 256, and this shear stress enhances fragmentation and the removal rate of fibrous tissue.

It will be noted that the teeth 274 and 276 at the ends of the first row 252 are truncated while the teeth in the second row are full in the embodiment shown in FIGS. 6A and 6B.

Figure 6C:
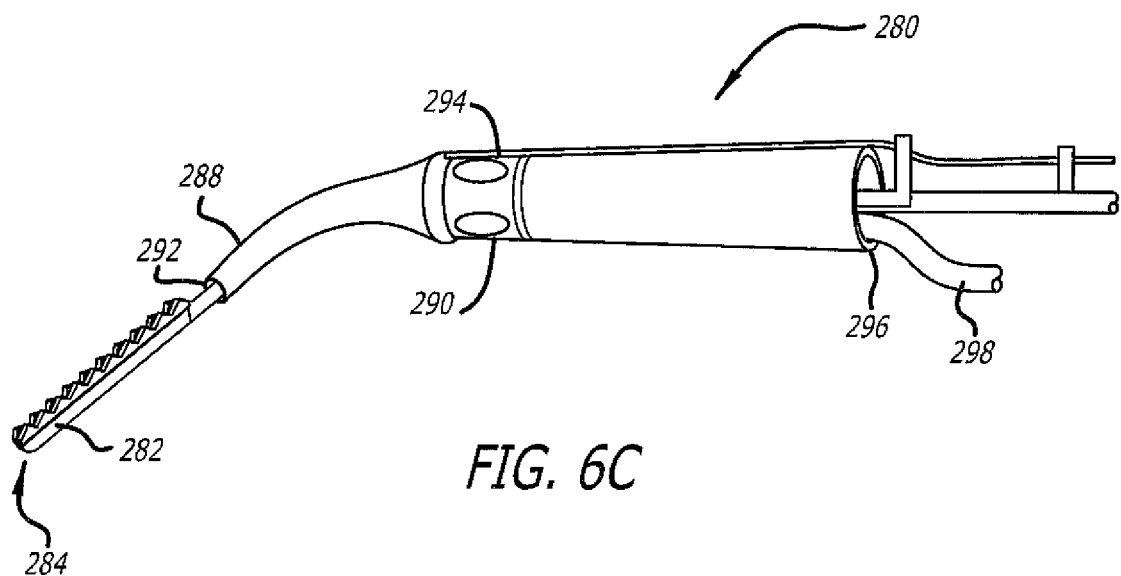
FIG. 6C shows a different embodiment of an ultrasonic horn having an shear stress ultrasonic cutting blade mounted at the distal end of a body member as in other figures but in this figure there is also shown an irrigation system comprising a flue surrounding part of the horn just proximal to the cutting blade, the flue being open at its distal end so that irrigation fluid will be distributed down the blade by gravity in this embodiment.

FIG. 6C shows a different embodiment of an ultrasonic horn 280 having a cutting blade 282 mounted at the distal end 284 as in other figures, but in this figure there is also shown an irrigation system 286 comprising a flue 288 surrounding the part of the body 290 of the horn just proximal to the cutting blade, the flue being open 292 at its distal end so that irrigation fluid will be distributed down the blade by gravity. A feed tube 294 is used to conduct coolant to the flue from a source (not shown) at the proximal end 296 of the body 290. A tube for aspiration 298 is also shown at the proximal end of the body 290.

In the figures, the distal lands have been called "distal" because they face in the distal longitudinal direction. The rows shown in the figures are linear and not annular. Likewise, the proximal lands have been called "proximal" because they fact in the proximal longitudinal direction. In the embodiments shown, the rows of teeth are touching each other although they are termed to be separate rows. The peaks of the lands are shown in the figures as being sharp but depending on their use, they may be blunted.

Figure 5D:
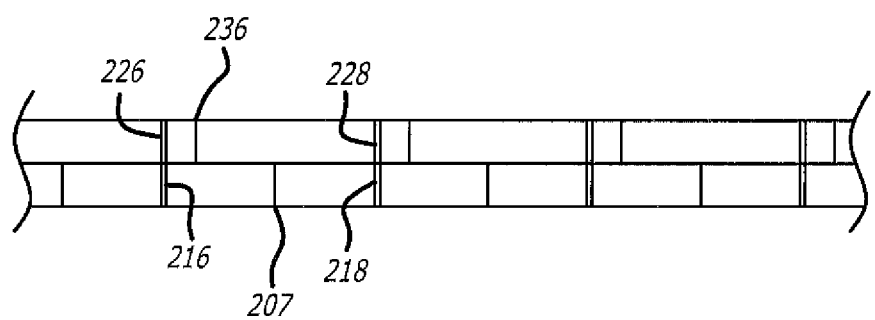
FIG. 5D is a top view of a cutting blade in accordance with aspects of an embodiment of the invention showing the roots and lands of both rows of teeth, in particular showing that the roots of the teeth of one row are aligned with the roots of the teeth of the adjacent row but with the lands of one row having a different angle from the lands of the adjacent row to form shear stress fields.
Figure 6D:
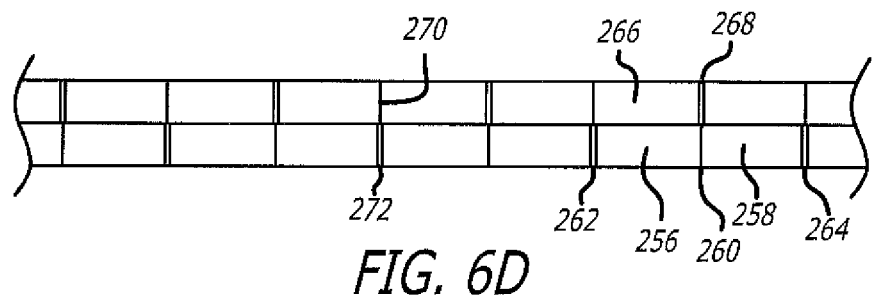
FIG. 6D is a top view of the cutting blade of the embodiment of FIGS. 6A and 6B showing that the roots of one row of teeth are offset from the roots of the adjacent second row of teeth. In particular, the roots of one row are aligned with the peaks of the adjacent row thereby forming an angular difference between adjacent proximal and distal lands of 90°.

FIGS. 5D and 6D are top views of the relative positioning of the teeth between rows. These are but two embodiments. The alignment of offset of the teeth in one row to the teeth in another row can be altered in accordance with the application of the cutting blade. The angles of the teeth in both rows can be set to achieve different angles to develop the shear stress fields as desired.

It should be noted that the relative positioning between the teeth of one row to the teeth of another row can be selected as desired to achieve the cutting results needed. Additionally, although shown in the embodiments as having only two rows of teeth, the cutting blade may have more than two rows, as is needed for the purpose at hand.

It is known that the angle of refraction of the longitudinal wave can be ideally calculated based on Snell's Law, and it is dependent on the incident angle and difference in acoustic velocity of titanium (the material of the horn in one embodiment) and the medium or media encountered at the boundary, e.g., soft tissue, fibrous muscle, water, etc. An illustration of the ultrasonic horn to tissue interface for adjacent lands of opposite angles is provided in FIGS. 7-10 for an assumed dominantly directed extensional wave along the longitudinal axis of the surgical tip. For a +45° and −45° interface of the titanium lands 166 and 167 of opposite angles to tissue 180, the refracted longitudinal wave angles were calculated for air, water, soft tissue, muscle, and bone employing representative material properties from the literature. Most pertinent a 13° refracted longitudinal wave angle is calculated for titanium to muscle.

Figure 7:
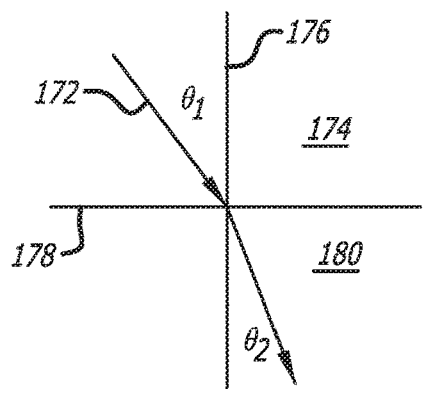
FIG. 7 is a basic diagram showing the operation of Snell's law at the interface of two different materials, one of which is the material of the shear stress ultrasonic cutting blade of the ultrasonic horn and the other of which is the material of target tissue.

In FIG. 7, the basic principle of refraction is illustrated. The ultrasonic energy 172 is propagating in titanium 174 at an angle of 0°, to the ordinate axis 176. Upon reaching the boundary 178 (abscissa axis) with fibrous tissue 180, the ultrasonic energy 172 is refracted by 13°. Therefore $\theta_2 = \pm 13°$ as measured from the normal to the interface.

Figure 8:
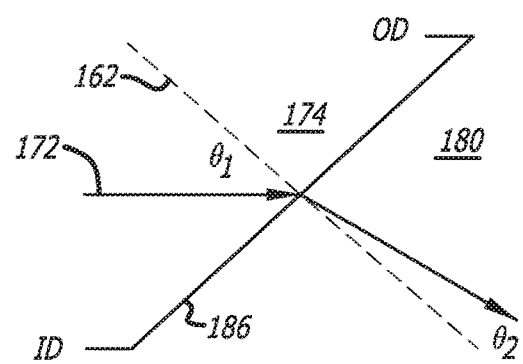
FIG. 8 is a schematic diagram showing the refraction of ultrasonic energy from a land of a tooth of the cutting blade located at the distal end of an ultrasonic horn, the land being oriented at a first angle of +45°.

FIG. 8 presents a diagram of a titanium land 186 having an inner diameter ID and an outer diameter OD. Ultrasonic energy 172 is propagating through the land at an tingle of $\theta_1 = +45°$ to the centerline 162 through the land. Upon reaching the boundary 186 with fibrous tissue 180, refraction occurs and the ultrasonic energy then has an angle of $\theta_2$ with the centerline 162, where $\theta_1 \neq \theta_2$.

Figure 9:
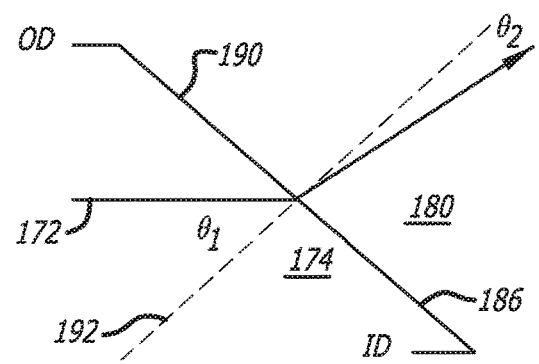
FIG. 9 is a schematic diagram showing the refraction of ultrasonic energy from a land of a tooth of the cutting blade located at the distal end of an ultrasonic horn, the land being oriented at a second angle of −45° (which is opposite the first angle)

FIG. 9 presents a diagram of a titanium land 190 having the opposite land angle than that of the land 186 in FIG. 7. The land 190 has an inner diameter ID and an outer diameter OD. Ultrasonic energy 172 is propagating through the land at an angle of $\theta_1 = -45°$ to the centerline 192 through the land. Upon reaching the boundary 186 with fibrous tissue 180, refraction occurs and the ultrasonic energy then has an angle of $\theta_2$ with the centerline 192, where $\theta_1 \neq \theta_2$.

Figure 10:
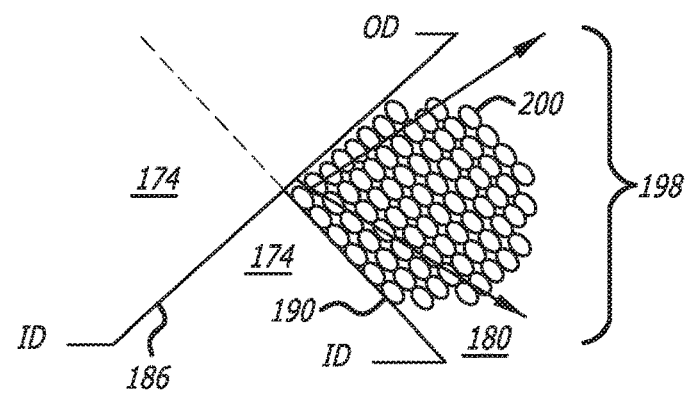
FIG. 10 is an illustration of the propagation of a shear stress field through adjacent cells located about the apex of the land members of FIGS. 8 and 9 that results when the refracted waves of the first land member (FIG. 8) are coupled with the refracted waves of the second and adjacent land member (FIG. 9)

FIG. 10 is a drawing showing the land 186 of FIG. 8 in front of the land 190 of FIG. 9 with the refracted ultrasonic energy of each creating a shear stress field 198. Due to the adjacent lands 186 and 190 being of opposite angles, there will be component waves causing shear 198. Refracted longitudinal waves of different directions produce a shear stress field, especially at the intersection of opposite angled lands, and this shear stress enhances fragmentation and removal rate of fibrous tissue 180. Adjacent cells or particles 200 about the intersection of the lands could experience displacement or particle motion with 64° of shear. It is important to note that due to the adjacent lands being of opposite angles (in this case +45° and −45°), there will always be component waves propagating at opposite angles that will subject the fibrous tissue to shear stress.

In a preferred embodiment, the shear stress tip implementation of adjacent opposite angled lands 186 and 190 does not compress tissue 180. Ultrasound energy 172 from adjacent opposite angled lands does not cancel due to destructive interference. However, opposing faces would cancel ultrasound energy due to destructive interference and would cause compression of tissue.

It has been found that although a shear wave component may exist and aid in fragmentation when coupled via solids, refracted longitudinal waves exist and will couple even in liquid, such as water or saline solution supplied as irrigation liquid via a surgical tip flue or another channel. Shear waves will not propagate directly in gases and liquids. Shear stress is not wholly or largely dependent on coupling of a shear wave, but rather would be promoted by refracted longitudinal waves of opposite angles.

Increasing the angle to 60° from 45° between the lands 166, 167 and the tissue would typically increase shear angle but reduce transmitted particle displacement. Reducing the land angle between the lands 166, 167 and the tissue from 45° to 30° would reduce shear angle but increase particle displacement. Given that particle displacement calculated exceeds 130% for angles from 30° to 60°, the selection of angle may be dominated by shear angle and ease of manufacturing. Alternative angles could be selected without substantially deviating from the shear stress tip principle of operation.

Figure 11:
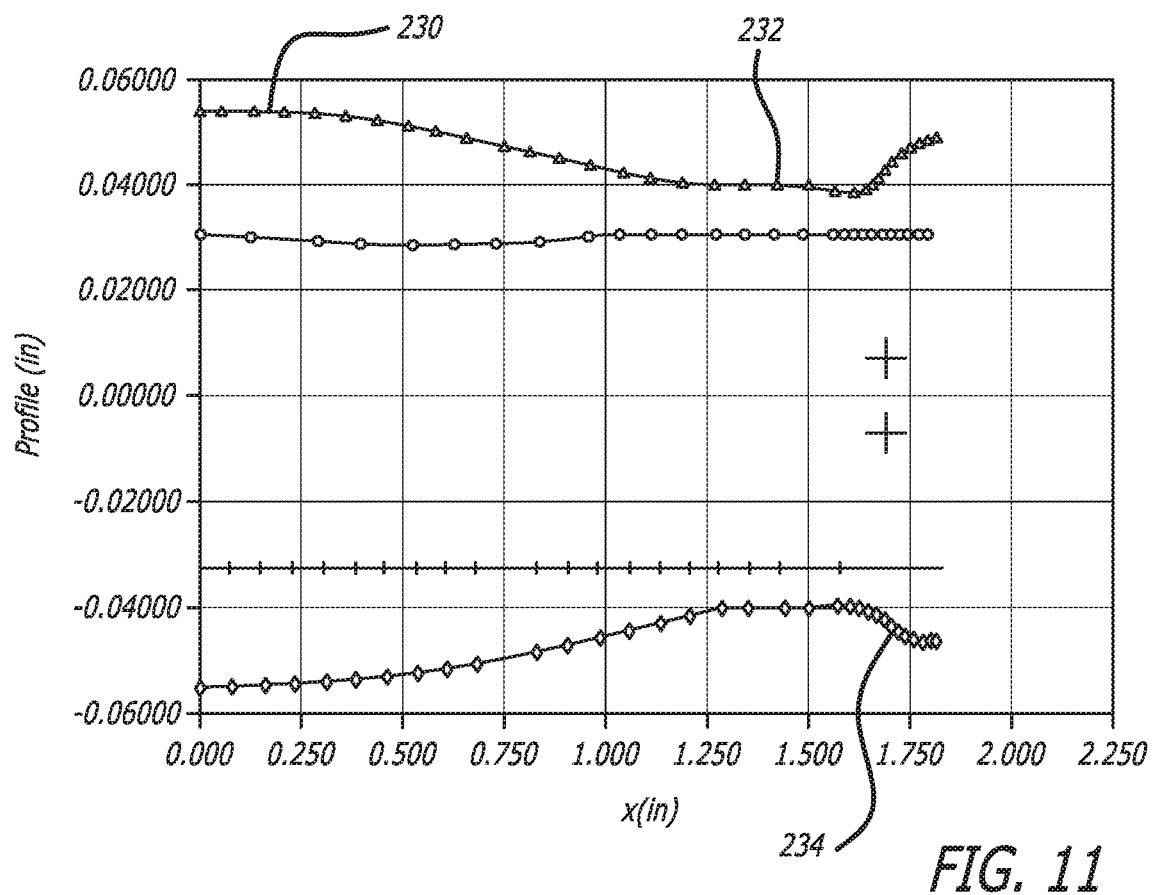
FIG. 11 is a graph of the ultrasonic horn radius versus horn length for a target frequency of 36 kHz shown in area function of the Gaussian shape.

FIG. 11 illustrates a shear stress tip profile 230. Area function of the Gaussian is shown, and it influences the resonant frequency and the mechanical gain. A blend is provided to a short straight section 232. A flared exponential profile 234 of the home expands the wall thickness suitably for machining of the distal end of the shear stress tip comprising a plurality of lands as shown in FIGS. 5 and 6, as one embodiment.

Figure 12:
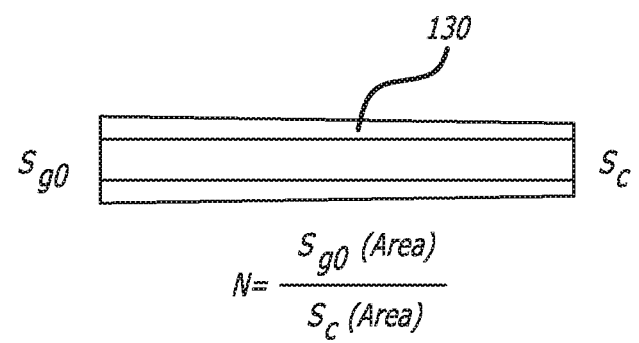
FIG. 12 presents a diagram of the shape of an ultrasonic horn.

In FIG. 12, the elongated member 130 is tapered such that the cross-sectional area $S_{go}$ is a maximum at the proximal end 136 interfacing with the transition segment 134 and is a minimum $S_c$, at the tip 132. An area function is defined as N where $N = S_{go}/S_c$, and is the area ratio of the Gaussian portion, and it establishes gain. The ultrasonic wave is supported by particle motion in the titanium. The particles are vibrating about their neutral position in a longitudinal or extensional wave. The particles do not move along the length of the horn, but only vibrate, just as a cork or bobber shows that a wave passes through water via the liquid. As the horn wall thickness decreases, more strain occurs in the metal as the particles move a greater distance about their neutral position. The displacement of the end of the horn is due to strain along the horn. All the particles supporting the wave are moving at the same resonant frequency. The greater the strain, the greater the velocity of the particles necessary to maintain the same frequency.

Mechanical gain in the ultrasonic horn 100 is maximized within acceptable stress limits of the titanium with stepped horn, Gaussian horn, blended short straight section, and flared exponential profiles. CUSA® (Integra Life Sciences Corporation, Plainsboro, N.J.) Ampulla (Gaussian) profile affords multiplying the gain of the stepped horn with a uniform distribution of stress, and this profile coupled with a blend to short straight section and flared exponential provide high-gain and forward propagation of ultrasound with minimal errant reflection or standing waves that could limit transmitted ultrasound, increase power requirements, or reduce horn stroke amplitude. These horn profiles promote high mechanical gain, forward propagation of ultrasound, and commensurate surgical tip distal-end stroke.

Stroke amplitude was not sacrificed in adapting to a larger wall thickness distal end for 36 kHz shear stress tip; in fact, prototype horn stroke exceeded the commercial baseline. This was accomplished with optimization of the Gaussian profile and blend to the straight section. Stroke peak-to-peak of the prototypes was 196 pm (0.0077 in) versus 183 pm (0.0072 in).

In one embodiment, pre-aspiration apertures or holes 150 (FIG. 1) are formed through opposing sides of the elongated member 130 wall on opposing sides of a straight or constant diameter portion. Pre-aspiration apertures may be employed in conjunction with the internal channel 146, which, as previously noted, extends from the proximal end 104 to the distal tip 132. The pre-aspiration holes 150 can be optionally used to suction a portion of the irrigation liquid employed through the channel to aid in cooling the tip. The pre-aspiration holes can also reduce misting caused by cavitation at the distal end of tip, thereby improving viewing via endoscopes or microscopes.

In terms of applications, the ultrasonic horn 100 is useful for cranial-based surgery, and when performing trans-sphenoidal or endoscopic-nasal approaches. The ultrasonic horns 100 and 101 of the present disclosure can be combined with irrigation and aspiration systems such as is disclosed in for example, FIG. 3 of U.S. Pat. No. 6,214,017 B1 to Stoddard et al., which as noted is incorporated by reference herein in its entirety. Irrigation in the internal channel 146 aids in cooling the material of the horn which is in flexure. Pre-aspiration holes 150 may also aid in cooling. The cooling capability can be enhanced by suctioning some portion of the irrigation liquid through the internal channel 146 of the horn 100 or 101 via pre-aspiration.

As used herein, "vacuum" is meant to include partial vacuum or lowered pressure. The term "angled inwardly" is meant to indicate that the angle is formed on the inside surface of the contact annulus. The term "angled outwardly" is meant to indicate that the angle is formed on the outside surface of the contact annulus. Additionally, the term "lands" is meant to refer to the surface commonly given this name in the art and is also meant to refer to other surfaces that perform the same function.

The word "comprise" and variations thereof, such as, "comprises" and "comprising" are to be construed in the normal patent law sense; i.e., an open, inclusive sense, which is as "including, but not limited to."

While the present invention has been described herein in terms of certain preferred embodiments, those skilled in the art will recognize that modifications and improvements may be made without departing from the scope of the invention. Moreover, while individual features of one embodiment of the invention may be discussed or shown in the drawings of the one embodiment and not in other embodiments, it should be apparent that individual features of one embodiment may be combined with one or more features of another embodiment or features from a plurality of embodiments.

FIG. 6D is a top view of the cutting blade of the embodiment of FIGS. 6A and 6B showing that the roots of one row of teeth are offset from the roots of the adjacent second row of teeth. In particular, the roots of one row are aligned with the peaks of the adjacent row thereby forming an angular difference between adjacent proximal and distal lands of 90°.

What is claimed is:

1. An ultrasonic horn configured for use with an ultrasonic surgical handpiece having a resonator that generates ultrasonic waves, the ultrasonic horn comprising:
   a body member having a proximal end, a distal end, and a longitudinal axis, the proximal end being adapted to connect to the handpiece and receive ultrasonic waves from the handpiece, and the body member configured to conduct the received ultrasonic waves to the distal end;
   an ultrasonic blade located at the distal end, the ultrasonic blade being non-annular and having a linear cutting surface on which are located a first row of a plurality of teeth and a second row of a plurality of teeth, the cutting surface configured so that the first row and the second row of teeth are located side-by-side one another and both first and second rows are parallel to the longitudinal axis, each tooth of the pluralities of teeth in the first and second rows having a root located at the cutting surface, a peak, and a land located outward from the cutting surface, each land configured to propagate ultrasonic waves outwardly from the distal end;
   wherein the plurality of teeth in the first row and the plurality of teeth in the second row are located and oriented in relation to each other on the cutting surface so that the ultrasonic waves propagated outwardly by the lands of the teeth of the first row intersect the ultrasonic waves propagated outwardly by the lands of the teeth of the second row to create shear stress fields;
   wherein roots of the teeth of the first row of teeth are not interleaved with roots of the teeth of the second row of teeth and the roots of the respective rows of teeth do not cross a plane extending between the first row of teeth and the second row of teeth, wherein the plane bisects the longitudinal axis from a proximal end of the ultrasonic blade to a distal end of the ultrasonic blade;
   wherein the roots of the first row of teeth and the roots of the second row of teeth are located transverse to the longitudinal axis and each peak of each tooth of the first row of teeth is offset from each peak of each tooth of the second row of teeth transverse to the longitudinal axis.

2. The ultrasonic horn of claim 1 wherein the linear cutting surface has a first width on which the adjacent first and second rows of teeth are located, and wherein the blade has material under the linear cutting surface that is undercut whereby a second width of the blade at the undercut is less than the first width of the blade at the cutting surface.

3. The ultrasonic horn of claim 1 wherein the plurality of teeth of the first row are located on the cutting surface so that the lands of the teeth of the first row extend in the distal direction.

4. The ultrasonic horn of claim 1 wherein the roots of the first row of teeth and the roots of the second row of teeth are aligned transverse to the longitudinal axis at the cutting surface.

5. The ultrasonic horn of claim 4 wherein angles of the lands of the teeth in the first row are different from angles of the lands of the teeth in the second row.

6. The ultrasonic horn of claim 1 wherein the roots of the first row of teeth and the roots of the second row of teeth are offset transverse to the longitudinal axis at the cutting surface.

7. The ultrasonic horn of claim 6 wherein an angle of the lands of the teeth in the first row of teeth and an angle of the lands of the teeth in the second row of teeth are different.

8. The ultrasonic horn of claim 7 wherein the angle of the lands of the teeth of the first row of teeth and the angle of the lands of the teeth of the second row of teeth are opposite angles.

9. The ultrasonic horn of claim 1 wherein the plurality of teeth in the first row are located at the cutting surface and oriented at an angle to the longitudinal axis so that ultrasonic waves propagating from the lands of the first row of teeth intersect ultrasonic waves propagating from the lands of the plurality of teeth in the second row of teeth which are also located at the cutting surface and oriented at an angle to the longitudinal axis so that shear fields are located transverse to the longitudinal axis.

10. The ultrasonic horn of claim 1 wherein the plurality of teeth in the first row are oriented so that their lands extend in the distal direction and the plurality of teeth in the second row are oriented so that their lands extend in the proximal direction.

11. The ultrasonic horn of claim 10 wherein the roots of the teeth in the first row are aligned transversely across the longitudinal axis with the roots of the teeth in the second row and the lands of the first row have a different angle from the lands in the second row.

12. The ultrasonic horn of claim 1 wherein the first and second rows are positioned on either side of the longitudinal axis in forming the linear cutting surface of the blade.

13. The ultrasonic horn of claim 10 wherein the roots of the teeth in the first row are offset from the roots of the teeth in the second row and the lands of the first row have the same but opposite angle in respect to the lands in the second row.

14. The ultrasonic horn of claim 1 wherein the first and second rows of teeth are linear rows.

15. An ultrasonic horn configured for use with an ultrasonic surgical handpiece having a resonator that generates ultrasonic waves, the ultrasonic horn comprising:
   a body member having a proximal end, a distal end, and a longitudinal axis, the proximal end being adapted to connect to the handpiece and receive ultrasonic waves from the handpiece, and the body member configured to conduct the received ultrasonic waves to the distal end; and an ultrasonic blade located at the distal end, the ultrasonic blade being non-annular and having a linear cutting surface on which are located two parallel linear rows of teeth, each row having a plurality of teeth, the rows being adjacent each other and positioned on either side of the longitudinal axis parallel therewith, each tooth having a root located at the cutting surface, a peak, and a land located outward from the cutting surface, each land configured to propagate ultrasonic waves outwardly;

wherein the lands of the first row of teeth and the lands of the second row of teeth are located and oriented in relation to the lands of the other row of teeth so that the respective ultrasonic waves propagated outwardly by the lands of one row intersect with the ultrasonic waves propagated outwardly by the lands of the other row to create shear stress fields;

wherein roots of the teeth of a first row of teeth of the parallel linear rows of teeth are not interleaved with roots of the teeth of a second row of teeth of the parallel linear rows of teeth and the roots of the respective parallel linear rows of teeth do not cross a plane extending between the first row of teeth and the second row of teeth, wherein the plane bisects the longitudinal axis from a proximal end of the ultrasonic blade to a distal end of the ultrasonic blade;

wherein the roots of the first row of teeth and the roots of the second row of teeth are located transverse to the longitudinal axis and each peak of each tooth of the first row of teeth is offset from each peak of each tooth of the second row of teeth transverse to the longitudinal axis.

16. The ultrasonic horn of claim 15 wherein:
the locations of the roots in the first linear row of teeth are offset from the locations of the roots in the second linear row of teeth transverse to the longitudinal axis.

17. The ultrasonic horn of claim 15 wherein:
the locations of the roots in the first linear row of teeth are aligned with the locations of the roots in the second linear row of teeth transverse to the longitudinal axis.

18. The ultrasonic horn of claim 15 wherein the plurality of teeth in the first row are located at the cutting surface and oriented at an angle to the longitudinal axis so that ultrasonic waves propagating from the lands of the first row of teeth intersect ultrasonic waves propagating from the lands of the plurality of teeth in the second row of teeth which are also located at the cutting surface and are oriented at an angle to the longitudinal axis so that shear fields are located transverse to the longitudinal axis.

19. The ultrasonic horn of claim 17 wherein the lands of the first parallel linear row of teeth have a different angle from the lands in the second parallel linear row of teeth.

20. The ultrasonic horn of claim 15 wherein the linear cutting surface has a first width on which the adjacent first and second parallel linear rows of teeth are located, and wherein the blade has material under the linear cutting surface that is undercut whereby a width of the blade at the undercut is less than the width of the blade at the cutting surface.

21. A method of creating a shear stress field with ultrasonic energy comprising:
conducting ultrasonic energy through a body member from a proximal end of the body member to a distal end of the body member, the body member having a longitudinal axis; and propagating the conducted ultrasonic energy outwardly from the distal end of the body member through a first row of teeth and a second row of teeth that are both mounted to a cutting surface of a non-annular linear blade located at the distal end and are positioned adjacent each other, each tooth having a root located at the cutting surface, a peak, and a land located outward from the cutting surface;

wherein the step of propagating further comprises propagating the energy through first and second rows of teeth in which the roots of the teeth of the first row of teeth are not interleaved with roots of the teeth of the second row of teeth and the roots of the respective rows of teeth do not cross a plane extending between the first row of teeth and the second row of teeth, wherein the plane bisects the longitudinal axis from a proximal end of the ultrasonic blade to a distal end of the ultrasonic blade;

wherein the step of propagating further comprises propagating the energy through first and second rows of teeth in which the roots of the first row of teeth and the roots of the second row of teeth are located transverse to the longitudinal axis and each peak of each tooth of the first row of teeth is offset from each peak of each tooth of the second row of teeth transverse to the longitudinal axis; and wherein the step of propagating comprises propagating ultrasonic energy outwardly by each land in a direction that intersects propagated energy by the other land to thereby form a shear stress field.

22. The method of creating a shear stress field of claim 21 wherein the propagating step further includes propagating the conducted ultrasonic energy outwardly from the distal end of the body member through lands of a first row of teeth and through lands of a second row of teeth wherein the roots of the first row of teeth and the roots of the second row of teeth are aligned transverse to the longitudinal axis at the cutting surface.

23. The method of creating a shear stress field of claim 21 wherein the propagating step further includes propagating the conducted ultrasonic energy outwardly from the distal end of the body member through lands of first row of teeth and through lands of a second row of teeth wherein the roots of the first row of teeth and the roots of the second row of teeth are offset transverse to the longitudinal axis at the cutting surface.

* * * * *